(12) United States Patent
Fisher

(10) Patent No.: US 11,127,489 B2
(45) Date of Patent: Sep. 21, 2021

(54) DEVICE-BASED ACTION PLAN ALERTS

(71) Applicant: Accenture Global Services Limited, Dublin (IE)

(72) Inventor: Mark Jonathan Fisher, Hertford (GB)

(73) Assignee: Accenture Global Services Limited, Dublin (IE)

(*) Notice: Subject to any disclaimer, the term of this patent is extended or adjusted under 35 U.S.C. 154(b) by 1457 days.

(21) Appl. No.: 15/203,042

(22) Filed: Jul. 6, 2016

(65) Prior Publication Data

US 2017/0124262 A1 May 4, 2017

Related U.S. Application Data

(60) Provisional application No. 62/247,417, filed on Oct. 28, 2015.

(51) Int. Cl.
*G16H 40/63* (2018.01)
*G16H 20/10* (2018.01)
*G16H 40/67* (2018.01)
*G16H 10/20* (2018.01)
*G16H 40/20* (2018.01)
*G16H 15/00* (2018.01)

(52) U.S. Cl.
CPC ............ *G16H 10/20* (2018.01); *G16H 20/10* (2018.01); *G16H 40/20* (2018.01); *G16H 40/63* (2018.01); *G16H 40/67* (2018.01); *G16H 15/00* (2018.01)

(58) Field of Classification Search
CPC ........ H04L 51/26; G06Q 10/10; G16H 10/20; G16H 10/60; G16H 40/20; G16H 40/63; G16H 40/67; G16H 50/20; G16H 50/30; G16H 15/00; G16H 20/10
See application file for complete search history.

(56) References Cited

U.S. PATENT DOCUMENTS

| 7,704,214 | B2 | 4/2010 | Abraham-Fuchs et al. |
| 8,807,131 | B1 | 8/2014 | Tunnell et al. |
| 2006/0184800 | A1* | 8/2006 | Rosenberg ............... G07C 9/37 713/186 |

(Continued)

OTHER PUBLICATIONS

Howard et al, Electronic Monitoring of Adherence to Inhaled Medication in Asthma, 2014, Current Respiratory Medicine Reviews, 10, 50-63 (Year: 2014).*

(Continued)

*Primary Examiner* — Gregory Lultschik
(74) *Attorney, Agent, or Firm* — Harrity & Harrity, LLP

(57) ABSTRACT

A device may provide a user interface with which to provide an action plan. The device may detect one or more interactions with the user interface associated with identifying one or more portions of the action plan. The action plan may include information regarding a treatment plan for a patient. The device may parse the action plan to identify a set of prompts and/or a set of actions that are to be performed based on a set of triggers. The set of prompts may be related to a clinically validated questionnaire for a particular condition. The device may detect a particular trigger, of the set of triggers, after parsing the action plan. The device may provide, for display via the user interface, a particular prompt, of the set of prompts, or transmit data to perform a particular action, of the set of actions, based on detecting the particular trigger.

20 Claims, 6 Drawing Sheets

(56) References Cited

U.S. PATENT DOCUMENTS

| | | | |
|---|---|---|---|
| 2007/0279211 A1 | 12/2007 | Fenske et al. | |
| 2007/0288266 A1 | 12/2007 | Sysko et al. | |
| 2009/0163774 A1 | 6/2009 | Thatha et al. | |
| 2009/0167531 A1 | 7/2009 | Ferguson | |
| 2011/0077971 A1 | 3/2011 | Surwit et al. | |
| 2011/0166880 A1 | 7/2011 | Keynan et al. | |
| 2011/0184250 A1 | 7/2011 | Schmidt et al. | |
| 2011/0201901 A1* | 8/2011 | Khanuja | A61B 5/7275 600/300 |
| 2011/0227739 A1 | 9/2011 | Gilham et al. | |
| 2013/0117696 A1 | 5/2013 | Robertson et al. | |
| 2013/0346090 A1 | 12/2013 | Brincat et al. | |
| 2014/0023998 A1 | 1/2014 | Thompson et al. | |
| 2014/0122122 A1 | 5/2014 | Cooper et al. | |
| 2014/0129249 A1 | 5/2014 | Nkoy et al. | |
| 2015/0081334 A1 | 3/2015 | Dulin et al. | |
| 2015/0100335 A1* | 4/2015 | Englehard | A61M 15/008 705/2 |
| 2015/0112707 A1 | 4/2015 | Manice et al. | |
| 2015/0120320 A1 | 4/2015 | Fateh | |
| 2015/0358821 A1* | 12/2015 | Heredia | H04W 4/50 455/411 |
| 2016/0162645 A1* | 6/2016 | Bornhorst | G16H 70/20 705/3 |

OTHER PUBLICATIONS

Extended European search report corresponding to EP 16193447.6, dated Feb. 15, 2017, 10 pages.
Propeller, "How it Works," https://www.propellerhealth.com/how-it-works/, Feb. 26, 2016, 15 pages.
MyAsthma, "About the MyAsthma programme," https://myasthma.com/en/about-myasthma, Dec. 23, 2011, 2 pages.
AsthmaMD, "Features," http://www.asthmamd.org/features/, Jun. 11, 2014, 3 pages.
AsthmaSense, "Meet AsthmaSense Cloud," http://asthmasense.com/, Feb. 20, 2014, 2 pages.
Centre for Global eHealth Innovation, "breathe: A mobile asthma self-management application for consumers," http://ehealthinnovation.org/whatwedo/projects/breathe-a-mobile-asthma-self-management-application-for-consumers/, Oct. 26, 2012, 1 page.
Craven et al., "Towards a protocol for the development of mobile health Apps for patient self-monitoring," https://www.researchgate.net/profile/Michael_Craven2/publication/257819037_Towards_a_protocol_for_the_development_of_mobile_health_Apps_for_patient_self-monitoring/links/0c960525e76e4ea055000000.pdf, Jun. 2013, 2 pages.
ClinicalTrials, "A Pilot and Feasibility Study of Mobile-Based Asthma Action Plans," https://clinicaltrials.gov/ct2/show/NCT01514760, Feb. 17, 2016, 4 pages.
Burnay et al., "Challenges of a Mobile Application for Asthma and Allergic Rhinitis Patient Enablement—Interface and Synchronization," https://www.researchgate.net/profile/Joao_Fonseca5/publication/233873828_Challenges_of_a_Mobile_Application_for_Asthma_and_Allergic_Rhinitis_Patient_Enablement-Interface_and_Synchronization/links/0c96052aa46bf5d2b7000000.pdf, Jan. 2013, 7 pages.
Juniper et al., "Development and validation of a questionnaire to measure asthma control," http://erj.ersjournals.com/content/14/4/902.long, Oct. 1, 1999, 6 pages.
LifeMap Solutions, "Asthma Health," http://www.lifemap-solutions.com/products/asthma-health-app/, Mar. 10, 2015, 7 pages.
National Asthma Council Australia, "Asthma Buddy Phone Apps," http://www.nationalasthma.org.au/health-professionals/asthma-action-plans/asthma-buddy-phone-apps, Sep. 7, 2013, 2 pages.
Sunovion Pharaceuticals Inc., "Resource Center," http://copdtogether.com/resource-center/tools-resources.html, Oct. 30, 2014, 4 pages.
GlaxoSmithKline, "HealthCoach4Me," http://www.gskforyou.com/healthcare-resources/health-coach-4-me.html, Apr. 5, 2010, 1 page.
Apple, "Research and CareKit," http://www.apple.com/researchkit/, Mar. 21, 2016, 14 pages.

* cited by examiner

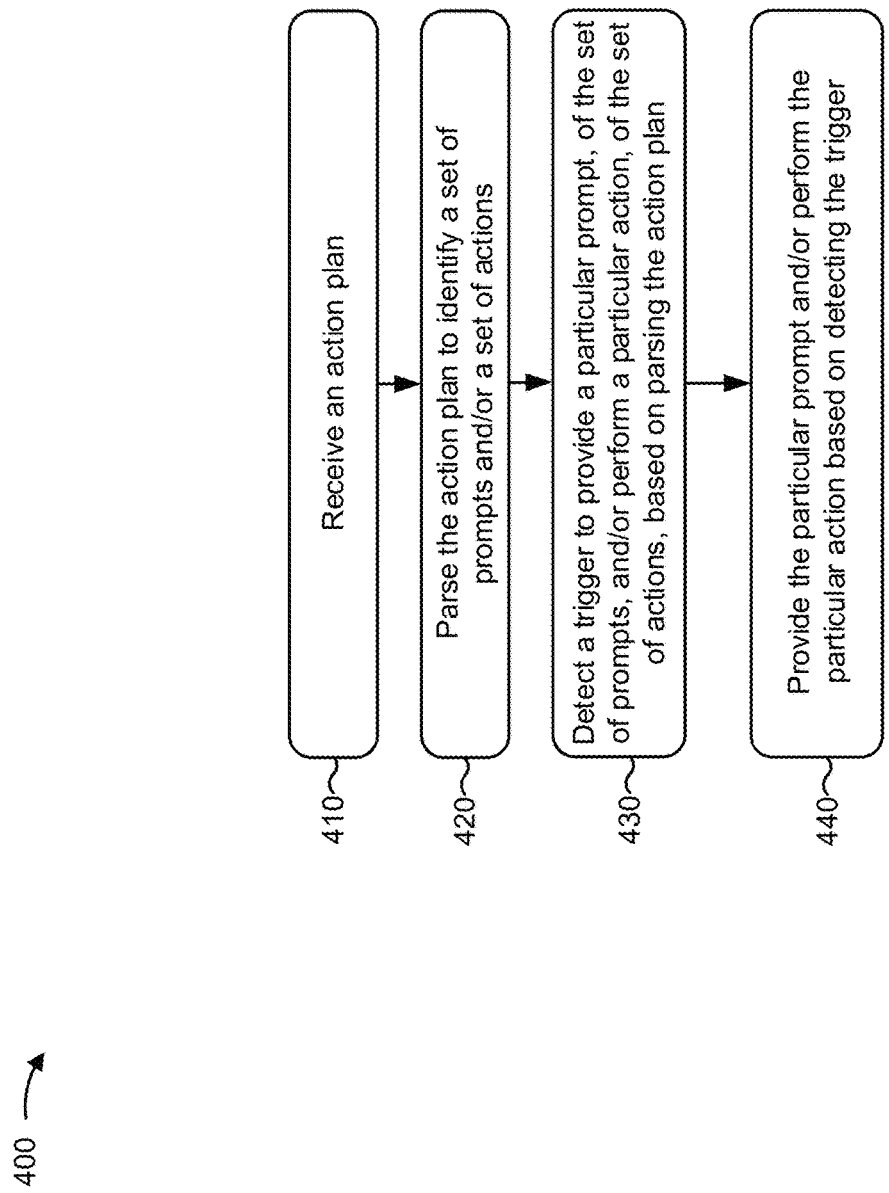

DEVICE-BASED ACTION PLAN ALERTS

RELATED APPLICATION(S)

This application claims priority under 35 U.S.C. § 119 to U.S. Provisional Patent Application No. 62/247,417, filed on Oct. 28, 2015, the content of which is incorporated by reference herein in its entirety.

BACKGROUND

A first party may desire that a second party comply with an action plan. For example, a doctor and a patient may agree on a treatment plan for a condition, such as an asthma-related condition or the like. The doctor may identify the treatment plan during an appointment with the patient, and may prescribe medicine associated with the treatment plan, such as a preventer inhaler, a reliever inhaler, or the like. The doctor may desire that the patient accurately follows the treatment plan; however, patients may have low compliance rates with the treatment plan for a number of reasons. For example, the patient may not adequately self-monitor symptoms, may forget to take medications as prescribed, may fail to recognize onset of crisis breathing episodes, or the like. As a result, desired asthma treatment plans may not be adhered to by patients.

SUMMARY

According to some possible implementations, a non-transitory computer-readable medium may store one or more instructions that, when executed by one or more processors, may cause the one or more processors to identify a group of prompts related to a patient action plan. The patient action plan may be created by a doctor in consultation with a patient. The one or more instructions, when executed by one or more processors, may cause the one or more processors to identify a trigger related to providing the group of prompts for display. The one or more instructions, when executed by one or more processors, may cause the one or more processors to monitor a data stream to detect the trigger based on identifying the trigger. The one or more instructions, when executed by one or more processors, may cause the one or more processors to receive, based on monitoring the data stream, data indicating that a set of criteria associated with the trigger is satisfied. The one or more instructions, when executed by one or more processors, may cause the one or more processors to provide a first prompt, of the group of prompts, for display via a user interface based on the data indicating that the set of criteria associated with the trigger is satisfied. The one or more instructions, when executed by one or more processors, may cause the one or more processors to detect, based on an interaction with the user interface, a response to the first prompt. The response may be included in a set of possible responses. Each response, of the set of possible responses, may correspond to a potential second prompt of the group of prompts. The one or more instructions, when executed by one or more processors, may cause the one or more processors to communicate with a sensor to receive sensor data associated with the patient action plan. The sensor data may relate to a utilization of a medical device. The one or more instructions, when executed by one or more processors, may cause the one or more processors to select a particular second prompt, of the group of prompts, based on the response to the first prompt and the sensor data. The one or more instructions, when executed by one or more processors, may cause the one or more processors to provide the particular second prompt for display via the user interface.

According to some possible implementations, a device may include one or more processors. The one or more processors may provide a user interface with which to provide an action plan. The one or more processors may detect one or more interactions with the user interface associated with identifying one or more portions of the action plan. The action plan may include information regarding a treatment plan for a patient. The one or more processors may parse the action plan to identify a set of prompts and/or a set of actions that are to be performed based on a set of triggers. The set of prompts may be related to a clinically validated questionnaire for a particular condition. The one or more processors may detect a particular trigger, of the set of triggers, after parsing the action plan. The one or more processors may provide, for display via the user interface, a particular prompt, of the set of prompts, or transmit data to perform a particular action, of the set of actions, based on detecting the particular trigger.

According to some possible implementations, a method may include receiving, by a device, an action plan related to monitoring an asthma patient. The action plan may be associated with a clinically validated questionnaire. The method may include parsing, by the device, the action plan to identify a set of prompts and/or a set of actions. The set of prompts may be related to evaluating the asthma patient based on the clinically validated questionnaire. The set of actions may be related to providing alerts to a set of entities based on evaluating the asthma patient. The method may include detecting, by the device, a trigger to provide a particular prompt, of the set of prompts or perform a particular action of the set of actions. The method may include providing, by the device, the particular prompt or performing the particular action based on detecting the trigger.

BRIEF DESCRIPTION OF THE DRAWINGS

FIG. 4 is a flow chart of an example process for providing device-based action plan alerts.

DETAILED DESCRIPTION

The following detailed description of example implementations refers to the accompanying drawings. The same reference numbers in different drawings may identify the same or similar elements.

A first party may identify a set of actions (e.g., an action plan) for a second party. For example, a health care professional (e.g., a doctor, a nurse, a pharmacist, an insurer, a provider, or the like) may develop a patient action plan in consultation with a patient. The patient action plan may include a treatment plan, such as a prescription for a particular type of medicine. For example, for a patient suffering from asthma-related symptoms, a doctor may identify a particular treatment plan for asthma-related symptoms, such as usage of a preventer inhaler, a reliever inhaler, or the like.

The doctor and the patient may discuss the patient action plan during an appointment, and the patient may be expected to follow the patient action plan to maintain wellness and avoid a negative health outcome. However, a doctor may fail to adequately describe the patient action plan and/or the patient action plan may be difficult for the patient to understand or follow without repeatedly contacting the doctor for clarification. Moreover, the patient may fail to contact the doctor for clarification for one or more reasons, such as inconvenience, failure to recognize that clarification is needed, or the like. Moreover, the patient may rarely record information regarding health status, resulting in the doctor having incomplete information from which to adjust the patient action plan when the patient does visit the doctor.

Implementations, described herein, may provide periodic alerts to ensure that a patient follows an action plan (e.g., a patient action plan related to monitoring an asthma patient). Moreover, based on receiving input from the patient regarding a condition of the patient (e.g., medication consumption, symptomology, symptom severity, clinically relevant measurements, or the like), the treatment plan and the periodic alerts may be automatically and dynamically adjusted, thereby facilitating effective and ongoing patient management. Moreover, based on ensuring that the patient is providing detailed tracking of symptoms (e.g., asthma-related symptoms) and/or compliance with a treatment plan and automatically providing the detailed tracking to a doctor, the doctor may be better positioned to alter a patient action plan to ensure patient health. In this way, patient compliance and health outcomes may be improved relative to a static treatment plan described to a patient by the patient's doctor.

Figure 1:
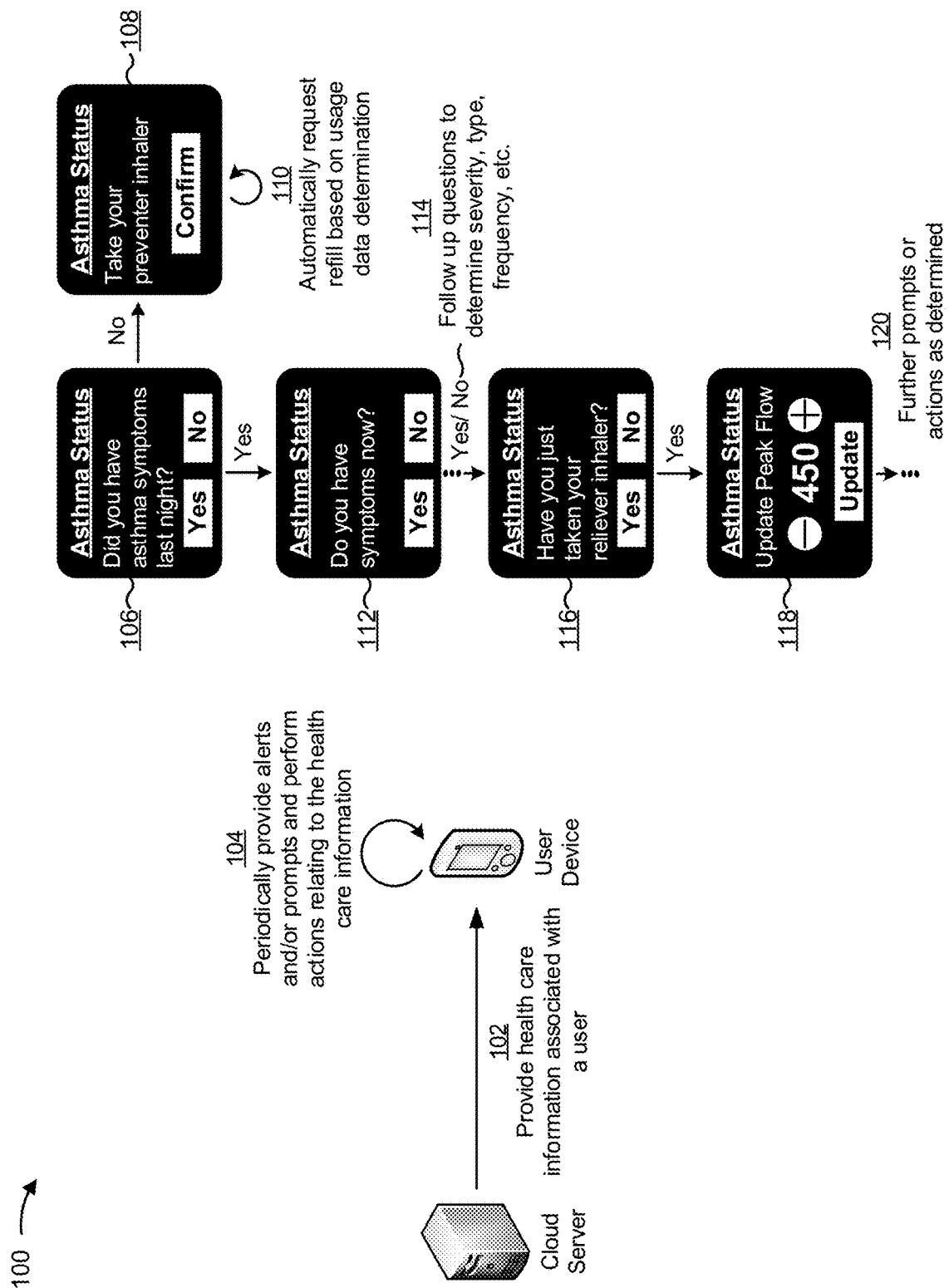
FIG. 1 is a diagram of an overview of an example implementation described herein.

FIG. 1 is a diagram of an overview of an example implementation 100 described herein. As shown in FIG. 1, example implementation 100 may include a cloud server and a user device. The cloud server may be associated with a health care professional (HCP), such as a doctor, a health management organization (HMO), a healthcare organization (HCO), a managed care consortium, a health care system, a hospital, a hospital network, or the like. For example, a doctor may provide a patient action plan including a set of recommendations for a patient as input to the cloud server, such as types of medications or the like.

As another example, the doctor or a nurse may input, via a user device (e.g., the user device, another user device, or the like) for transmission to the cloud server, an explanation of different medications included in the patient action plan, such as intended usage of a reliever inhaler (e.g., an inhaler prescribed for relief of asthma-related symptoms), a preventer inhaler (e.g., an inhaler prescribed to prevent an occurrence of asthma-related symptoms), or the like. Additionally, or alternatively, the doctor may include, in the patient action plan that is input to the cloud server, an explanation of actions that are to be performed in an emergency situation (e.g., a situation where symptoms have worsened). In another example, the user device and/or the cloud server may obtain information associated with defining portions of the patient action plan from a data structure. For example, the cloud server may automatically obtain a description of a medication included in the patient action plan from a server storing medication descriptions.

As shown by reference number 102, the cloud server may provide, to the user device, health care information associated with a user (e.g., the patient). For example, the cloud server may provide an application for execution via the user device, a user interface for display via the user device (e.g., via which a user may be presented health care information), data including secure (e.g., encrypted) health care information (e.g., for decryption and utilization by the user device), or the like.

As further shown in FIG. 1, and by reference number 104, the user device may periodically provide alerts and/or prompts and may perform actions relating to the health care information. For example, the user device may provide an alert requesting that a user complete a questionnaire regarding the user's health, may receive input associated with the questionnaire, and may provide an action alert indicating an action to be performed by the user, such as using an inhaler. In some implementations, the user device may determine when to provide an alert based on the treatment plan, a time of day, a sensor (e.g., a heartbeat sensor, a motion sensor, a sensor to detect allergens, a sensor to detect air quality, etc.), information gained from an external source, such as the Internet (e.g., air quality information, allergen information, etc.), or the like. For example, the user device may determine, based on a heartbeat sensor or motion sensor of the user device that the user has woken up from sleeping, and may provide a particular alert associated with a morning treatment plan. As another example, the user device may determine, based on a heartbeat sensor or motion sensor of the user device or based on feedback from an application operating on the user device (e.g., a workout tracking application) that the user has just finished exercising, and may provide a particular alert associated with a post-exercise treatment plan (e.g., for exercise induced asthma).

In some implementations, the user interface may be customized based on a characteristic of a patient. For example, for a child or adolescent patient, the user device may customize the user interface may utilize a simplified form of a question, such as prompting "are you coughing right now?" rather than prompting "are you currently suffering from asthma symptoms?" (e.g., as may be prompted for an adult). Similarly, for an elderly patient, the user device may customize the user interface to increase a text size of a prompt, a size of a button, or the like to reduce a difficulty in reading and responding to the prompts. In this way, the cloud server and/or the user device may utilize information regarding a patient to automatically and dynamically adjust a user interface improve a likelihood that the user is able to utilize the user interface relative to providing a static user interface for all users.

Reference numbers 106-120 provide an example of a set of prompts and a set of related alerts that may be provided by the user device, such as a set of questions associated with a morning treatment plan. For example, the user device may provide prompts associated with the Asthma Control Questionnaire, thereby ensuring clinically validated information gathering based on a clinically validated questionnaire. As shown by reference number 106, the user device may provide a prompt 106 regarding whether the user experienced asthma symptoms during the previous night. As shown by reference number 108, based on a user input of "No" to prompt 106, and based on the health care information, the user device may determine that the user is recommended to use a preventer inhaler, and may provide an alert associated with instructing the user to use the preventer inhaler.

As further shown in FIG. 1, and by reference number 110, the user device may monitor and/or estimate usage of the preventer inhaler (or another type of inhaler), and may automatically request a refill or replacement inhaler based on monitoring and/or estimating the usage (e.g., an amount of medication that has been utilized by the patient). For example, the user device may identify a volume of the preventer inhaler based on a prescription included in the health care information, may determine a first quantity of doses associated with the volume, and may track a second quantity of doses utilized by the user. In this case, the user device may perform a particular action, such as automatically requesting a refill of the prescription identified in the health care information based on the second quantity being within a threshold quantity of the first quantity. In this way, a likelihood that a user is unable to utilize the preventer inhaler as a result of failing to request a refill of a prescription is reduced relative to a user using the preventer inhaler without usage being tracked. In another example, the user device may provide an alert (e.g., to the user, to a doctor, to a pharmacist, etc.) that a refill of a prescription is necessary. In some implementations, the user device may track refills of the prescription, may determine that the user is seeking refills at a rate greater than a threshold rate (e.g., every week, every two weeks, etc.), and may automatically transmit an alert to a doctor that the user may need a consultation to adjust the prescription and/or the patient action plan, and may automatically schedule the consultation and cause calendar entries to be generated for the consultation. Similarly, the user device may determine that a condition of the patient differs by a threshold difference from an expected patient condition, and may transmit an alert to a doctor, and may automatically schedule a consultation. In this way, the user device may improve a likelihood that a doctor is able to intervene with a patient and alter a treatment plan relative to the doctor relying on patient recollection of inhaler usage and patient decisions to schedule an appointment.

As shown by reference number 112, based on a user input of "Yes" to prompt 106, the user device may provide another prompt 112 regarding whether the user is currently experiencing one or more asthma symptoms. As shown by reference number 114, based on a user input of "Yes" or "No" to prompt 112, the user device may generate one or more follow up prompts 114 intended to identify, for each asthma symptom experienced during the previous night or currently being experienced, a severity, a type, a frequency, or the like. In some implementations, the user device may selectively include or exclude one or more prompts of a set of prompts. For example, when a user indicates that they have not experienced any symptoms, the user device may exclude prompts relating to symptom severity, type, frequency, etc., and may proceed to other prompts. In this way, the user device reduces a quantity of time required to provide answers to the set of prompts relative to providing a fixed questionnaire, thereby increasing a likelihood that a user completes the set of prompts and reducing a battery usage associated with providing the set of prompts. Moreover, based on reducing the quantity of time that the user device is utilized to respond to the set of prompts, the user device may reduce battery usage, usage of processing resources, or the like relative to the user device being utilized for a static set of prompts.

In some implementations, the user device may automatically classify the one or more asthma symptoms. For example, the user device may classify the one or more asthma symptoms as being associated with a threshold severity, and may automatically notify another party, such as a doctor, a nurse, a pharmacist, an emergency medical technician, an ambulance dispatcher, or the like. In this way, the user device reduces a likelihood that a user contacts emergency services based on an incorrect belief that a symptom constitutes an emergency relative to requiring manual user contact. Alternatively, the user device reduces a likelihood that a user fails to contact emergency services based on an incorrect belief that a symptom does not constitute an emergency relative to requiring manual user contact.

Assume that based on the responses to the one or more prompts 114 and the health care information, the user device prompts the user to utilize a reliever inhaler. As shown by reference number 116, the user device provides a prompt 116 for the user to confirm use of the reliever inhaler. In another example, the user device may track utilization of the reliever inhaler and automatically request a refill of the reliever inhaler based on tracking the utilization. As shown by reference number 118, based on a user input of "Yes" to prompt 116, the user device may provide a prompt for the user to update a peak flow value associated with using the reliever inhaler. As shown by reference number 120, based on the user updating the peak flow value, the user device may provide one or more additional prompts, action alerts, or the like as determined based on the health care information. In another example, the user device may include a breath analyzer that the user device may utilize to obtain information regarding the user and determine one or more subsequent recommendations based on obtaining the information regarding the user.

As indicated above, FIG. 1 is provided merely as an example. Other examples are possible and may differ from what was described with regard to FIG. 1.

Figure 2:
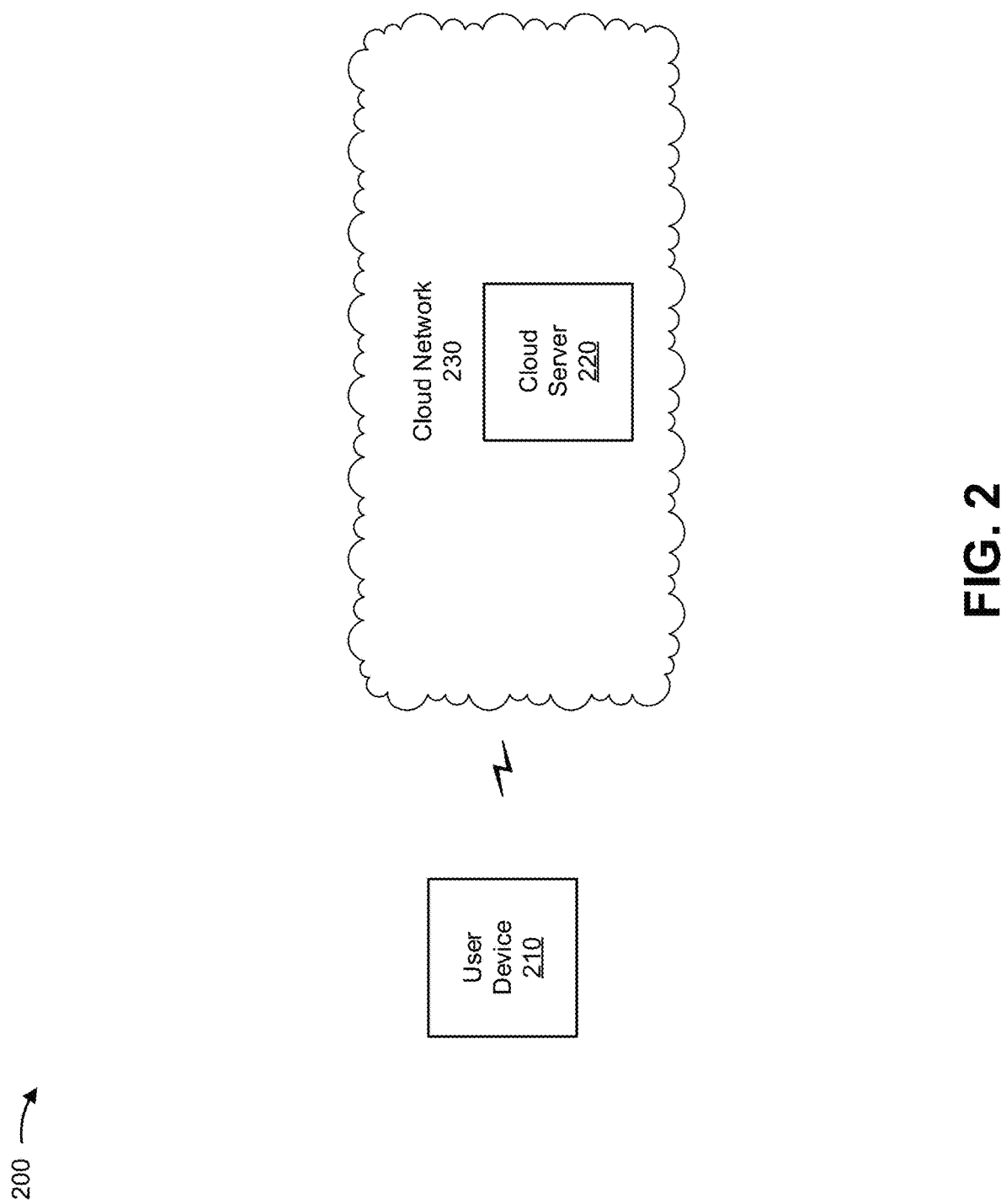
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a user device 210, a cloud server 220, and a cloud network 230. Devices of environment 200 may interconnect via wired connections, wireless connections, or a combination of wired and wireless connections.

User device 210 may include one or more devices capable of receiving, generating, storing, processing, and/or providing information associated with an action plan. For example, user device 210 may include a communication and/or computing device, such as a mobile phone (e.g., a smart phone, a radiotelephone, etc.), a laptop computer, a tablet computer, a handheld computer, a gaming device, a medical device, a wearable communication device (e.g., a smart wristwatch, a pair of smart eyeglasses, a wearable health or fitness tracker, etc.), or a similar type of device. In some implementations, user device 210 may be associated with a user interface for providing prompts and/or alerts.

In some implementations, user device 210 may be utilized by a particular type of user, such as an adult user, an adolescent user, a child user (e.g., a child 6-11 years of age), or the like, and may customize a user interface based on the particular type of user. In some implementations, user device 210 may be utilized by a user suffering from a particular severity of asthma (e.g., all severities of asthma, a subset of severities of asthma, etc.). In some implementations, user device 210 may connect to one or more medical devices, such as a Bluetooth enabled spirometer, a breath analyzer, a heartbeat sensor, or the like to automatically obtain medical information. In some implementations, multiple user devices 210 may be utilized. For example, a healthcare professional (e.g., a physician, a nurse, a pharmacist, or the like) may register a patient for alerts via a first user device 210, and the patient may receive alerts via a second user device 210. In some implementations, user device 210 may receive information from and/or transmit information to another device in environment 200.

Cloud server 220 may include one or more devices capable of storing, processing, and/or routing information associated with an action plan. For example, cloud server 220 may include a server, a medical device, or the like that provides health care information to user device 210 for utilization in ensuring compliance with a treatment plan by a user. In some implementations, cloud server 220 may include a communication interface that allows cloud server 220 to receive information from and/or transmit information to other devices in environment 200. While cloud server 220 is described as a resource in a cloud computing network, such as cloud network 230, cloud server 220 may operate external to a cloud computing network, in some implementations.

Cloud network 230 may include an environment that delivers computing as a service, whereby shared resources, services, etc. may be provided by cloud server 220 to store, process, and/or route information associated with an action plan. Cloud network 230 may provide computation, software, data access, storage, and/or other services that do not require end-user knowledge of a physical location and configuration of a system and/or a device that delivers the services (e.g., cloud server 220). As shown, cloud network 230 may include cloud server 220 and/or may communicate with user device 210 via one or more wired or wireless networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
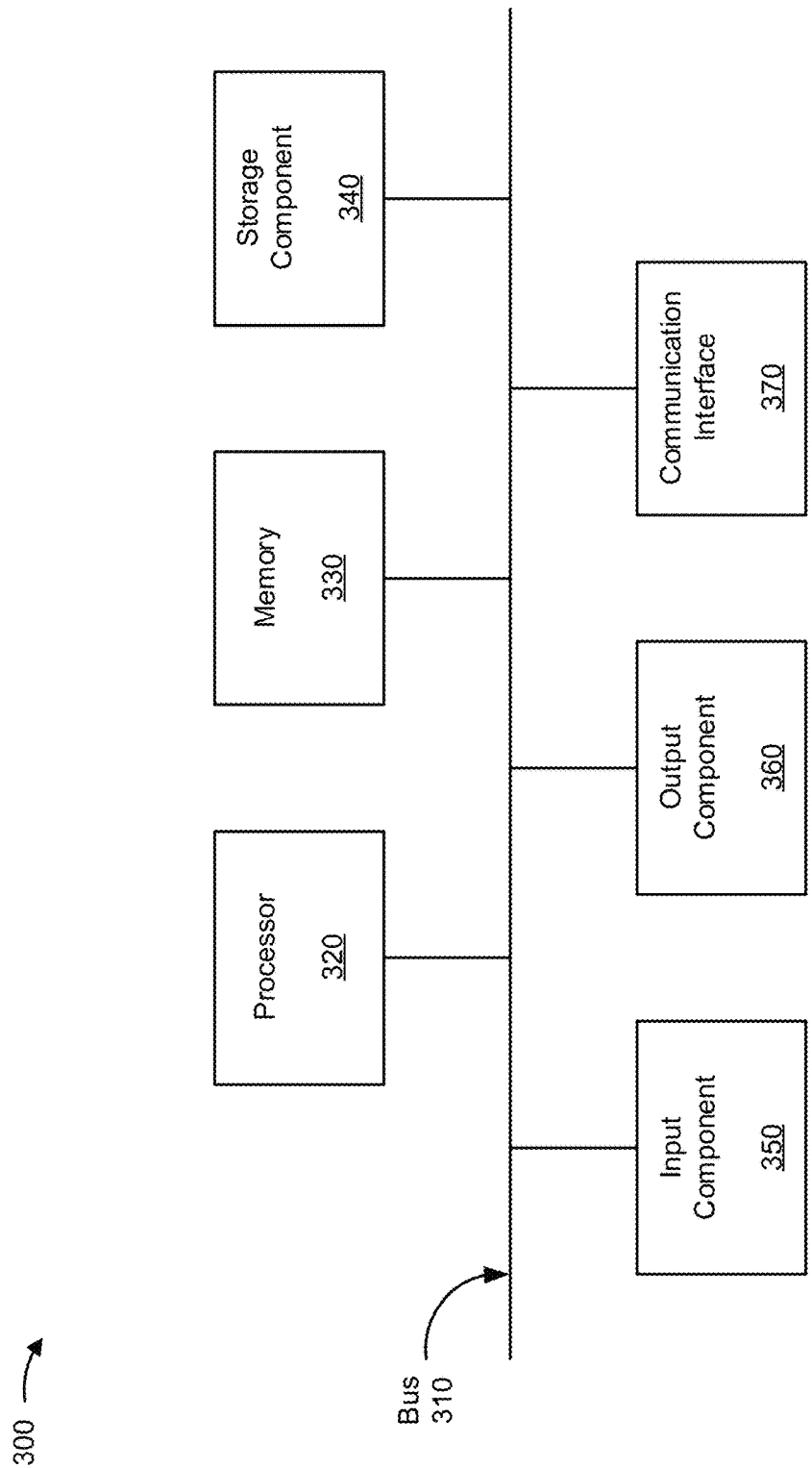
FIG. 3 is a diagram of example components of one or more devices of FIG. 2.

FIG. 3 is a diagram of example components of a device 300. Device 300 may correspond to user device 210 and/or cloud server 220. In some implementations, user device 210 and/or cloud server 220 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 may include a component that permits communication among the components of device 300. Processor 320 is implemented in hardware, firmware, or a combination of hardware and software. Processor 320 may include a processor (e.g., a central processing unit (CPU), a graphics processing unit (GPU), an accelerated processing unit (APU), etc.), a microprocessor, and/or any processing component (e.g., a field-programmable gate array (FPGA), an application-specific integrated circuit (ASIC), etc.) that interprets and/or executes instructions. In some implementations, processor 320 may include one or more processors that can be programmed to perform a function. Memory 330 may include a random access memory (RAM), a read only memory (ROM), and/or another type of dynamic or static storage device (e.g., a flash memory, a magnetic memory, an optical memory, etc.) that stores information and/or instructions for use by processor 320.

Storage component 340 may store information and/or software related to the operation and use of device 300. For example, storage component 340 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of non-transitory computer-readable medium, along with a corresponding drive.

Input component 350 may include a component that permits device 300 to receive information, such as via user input (e.g., a touch screen display, a keyboard, a keypad, a mouse, a button, a switch, a microphone, etc.). Additionally, or alternatively, input component 350 may include a sensor for sensing information (e.g., a global positioning system (GPS) component, an accelerometer, a gyroscope, an actuator, etc.). Output component 360 may include a component that provides output information from device 300 (e.g., a display, a speaker, one or more light-emitting diodes (LEDs), etc.).

Communication interface 370 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A non-transitory computer-readable medium is defined herein as a non-transitory memory device. A memory device includes memory space within a single physical storage device or memory space spread across multiple physical storage devices.

Software instructions may be read into memory 330 and/or storage component 340 from another non-transitory computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

FIG. 4 is a flow chart of an example process 400 for implementing action plan alerts. In some implementations, one or more process blocks of FIG. 4 may be performed by user device 210. In some implementations, one or more process blocks of FIG. 4 may be performed by another device or a group of devices separate from or including user device 210, such as cloud server 220 or the like.

As shown in FIG. 4, process 400 may include receiving an action plan (block 410). For example, user device 210 may receive the action plan. The action plan may refer to health care information (e.g., a treatment plan, a set of doctor recommendations, vitals information for a patient, or the like) for a patient suffering from a health condition, such as an asthma condition or the like. For example, user device 210 may receive an action plan including a set of instructions regarding medicine for the patient (e.g., a user of user device 210), such as information identifying the medicine (e.g., a prescription of an inhaler, such as a reliever inhaler, a preventer inhaler, or the like), information identifying a dosage of the medicine (e.g., a dosage for the inhaler), information identifying a set of criteria for determining whether to utilize the medicine (e.g., when the inhaler is to be used), or the like. Additionally, or alternatively, user device 210 may receive an action plan including information indicating a set of activities for mitigating the health condition, such as an exercise regimen, a set of dietary restrictions, a sleep schedule, or the like. Additionally, or alternatively, user device 210 may receive an action plan including information associated with the health condition, such as information identifying one or more symptoms of the health condition, information identifying a set of criteria for determining whether to contact a health care provider, information identifying answers to a set of common patient questions, information identifying contact information for a set of entities (e.g., a physician, an emergency management technician, a pharmacist), or the like.

In some implementations, user device 210 may receive an action plan that is associated with a particular questionnaire. For example, when user device 210 is utilized for an asthma patient, user device 210 may receive an action plan associated with the Asthma Control Questionnaire, such as an action plan that indicates a set of actions to be performed based on possible answers to questions of the Asthma Control Questionnaire. In this way, user device 210 ensures that information provided based on the action plan is clinically validated information.

In some implementations, user device 210 may receive the action plan from cloud server 220. For example, user device 210 may request that cloud server 220 provide the action plan for a user of user device 210, and user device 210 may receive the action plan as a response. Additionally, or alternatively, user device 210 may receive the action plan from a data structure. For example, user device 210 may include a data structure storing the action plan, and may obtain the action plan from the data structure based on a user interaction with user device 210 (e.g., a user activating a medical application of user device 210). In some implementations, user device 210 may receive the action plan via a user interface. For example, user device 210 may provide a standardized framework user interface that may be utilized to select the action plan and/or portions of the action plan (e.g., a set of user interface elements permitting a user, such as a doctor, a pharmacist, or the like, to select a dosage of an inhaler, from a set of potential portions of the action plan, such as a set of potential dosages of the inhaler). In this case, when a patient is registered for an appointment via an appointment system of cloud server 220, user device 210 may be caused to provide a user interface with which to receive information regarding the patient, information regarding a diagnosis, information regarding a treatment plan, or the like.

Further to the example, user device 210 may receive information identifying portions of the action plan via a user interface, and may compare the portions of the action plan with one or more other action plans (e.g., stored via cloud server 220). In this case, user device 210 may determine that an error exists in the action plan based on the action plan deviating by a threshold amount from the one or more other action plans, and may provide an alert to cause a user to correct the action plan. In this way, user device 210 reduces a likelihood of an error in the action plan, thereby reducing a likelihood of negative patient outcomes relative to failing to perform a comparison of the action plan with other action plans. Moreover, user device 210 reduces a likelihood that the user is required to repeatedly correct the action plan, thereby reducing a utilization of processing resources of user device 210.

In some implementations, user device 210 may receive the action plan based on registering a user profile for a user. For example, user device 210 may provide a user interface with which to receive information regarding a user (e.g., a name, a medical record identifier, etc.), and may establish a user profile for the user via cloud server 220 based on receiving the information via the user interface. In this case, user device 210 may receive the action plan that corresponds to the user from cloud server 220 (e.g., based on information identifying the user). In some implementations, user device 210 may receive the action plan based on performing a document analysis. For example, user device 210 may be utilized to capture an image of an action plan document, and may perform an analysis on the document (e.g., natural language analysis, text recognition analysis, optical character recognition analysis, semantic meaning analysis, or the like.) to identify portions of the action plan described by the document.

In some implementations, user device 210 may obtain contextual information associated with the action plan from one or more data structures based on information included in the action plan. For example, when user device 210 receives an action plan that includes a medication for utilization by a patient, user device 210 may obtain information regarding the medication from a pharmaceutical data structure (e.g., a database storing information identifying a type of the medication, a dosage for the medication, a set of allergies related to the medication, instructions for using the medication, contact information for a pharmacist fulfilling a prescription for the medication, or the like). Similarly, user device 210 may obtain information regarding a patient identified in the action plan (e.g., a user of user device 210) from a healthcare data structure (e.g., a hospital database that stores a patient medical history, contact information for a doctor, or the like).

In some implementations, user device 210 may receive an alteration to a stored action plan. For example, when user device 210 stores an action plan for a patient, and a doctor of the patient determines that an alteration is to be made to the action plan (e.g., a medication is to be altered, an exercise regimen is to be altered, etc.), user device 210 may receive information associated with altering the action plan, and may incorporate the information into the action plan. In this way, user device 210 ensures that the action plan can be dynamically altered to better manage needs of a patient relative to a static action plan. Moreover, based on dynamically altering an action plan, user device 210 reduces a utilization of processing resources, an amount of network traffic, and/or a utilization of memory resources relative to requiring a complete, new action plan be provided to replace the action plan.

As further shown in FIG. 4, process 400 may include parsing the action plan to identify a set of prompts and/or a set of actions (block 420). For example, user device 210 may parse the action plan to identify the set of prompts and/or the set of actions. In some implementations, user device 210 may utilize a processing technique to parse the action plan. For example, when the action plan is a natural language document that includes a natural language description of a set of actions that are to be performed to control asthma symptoms, user device 210 may utilize a natural language processing technique to identify the set of actions. Similarly, when user device 210 receives a version of the Asthma Control Questionnaire for utilization in analyzing a condition of a patient (e.g., a user), user device 210 may parse the version of the Asthma Control Questionnaire to identify a set of questions, a set of dependencies (e.g., a set of relationships between two or more questions), or the like. In this case, based on identifying the set of dependencies, user device 210 may determine an order for providing a set of prompts, one or more prompts that are to be omitted from a group of prompts based on possible responses to a portion of the group of prompts, or the like. In this way, user device 210 reduces a battery utilization and/or utilization of processing resources relative to providing each prompt of a group of prompts regardless of responses to each prompt.

In some implementations, user device 210 may generate the set of prompts based on parsing the action plan. For example, when user device 210 receives an action plan indicating a set of criteria for performing the set of actions, such as a particular symptom for which emergency management personnel are to be dispatched, user device 210 may generate a prompt associated with determining whether the set of criteria are satisfied (e.g., a prompt for determining whether the user is experiencing the particular symptom). In some implementations, user device 210 may determine a context for providing one or more prompts. For example, user device 210 may determine that one or more prompts are to be provided when a user wakes up in the morning. In this case, user device 210 may identify one or more sensors from which to receive data to determine that the user has woken up, and to trigger providing the one or more prompts. As another example, user device 210 may determine that one or more prompts are to be provided at a particular time of day, when user device 210 is located at a particular location, after detecting a user is exercising, based on receiving particular sensor data, or the like.

In some implementations, user device 210 may correlate one or more prompts to one or more actions. For example, user device 210 may determine, based on the action plan, that a particular response to a particular prompt is associated with performing a particular action. Similarly, user device 210 may determine that instructing a user to perform a particular action (e.g., using an inhaler) may correlate to providing a particular prompt (e.g., requesting that the user provide confirmation that the user has performed the particular action). Additionally, or alternatively, user device 210 may determine to communicate to receive information. For example, user device 210 may detect one or more actions corresponding to inhaler usage (e.g., orienting the inhaler for utilization) based on an accelerometer, and may determine to provide a prompt to confirm that the inhaler is utilized.

As further shown in FIG. 4, process 400 may include detecting a trigger to provide a particular prompt, of the set of prompts, and/or perform a particular action, of the set of actions, based on parsing the action plan (block 430). For example, user device 210 may detect the trigger to provide the particular prompt, of the set of prompts, and/or perform the particular action, of the set of actions, based on parsing the action plan. In some implementations, user device 210 may detect a trigger related to a time of day. For example, based on parsing the action plan (e.g., which may indicate that a patient is to take a preventer inhaler in the morning), user device 210 may determine, at the time of day, to provide the particular prompt and/or perform the particular action.

Additionally, or alternatively, user device 210 may detect the trigger based monitoring a data stream for sensor data. For example, based on parsing the action plan (e.g., which may indicate that a patient is to take a preventer inhaler after exercising), user device 210 may monitor a data stream of sensor device (e.g., a heartbeat sensor, an accelerometer measuring activity, or the like) to determine that the user is exercising. In this case, user device 210 may communicate with the sensor device to obtain sensor data, which user device 210 may process to determine that the user is exercising or that another trigger has been satisfied (e.g., that the user has woken up, that the user is coughing, that an air quality metric is less than an air quality metric threshold, that the user's heart rate satisfies a heart rate threshold, or the like).

In some implementations, user device 210 may detect the trigger to provide the particular prompt and/or perform the particular action based on providing another prompt and/or performing another action. For example, based on parsing the action plan, user device 210 may identify a group of prompts associated with a particular group of dependencies (e.g., a first type of response to a first prompt causes user device 210 to provide a second prompt and a second type of response to the first prompt causes user device 210 to provide a third prompt), and may determine that based on a particular response to a particular prompt, user device 210 is to provide another particular prompt. Similarly, user device 210 may determine that based on a particular response to the particular prompt, user device 210 is to perform a particular action. Similarly, user device 210 may determine that based on performing a particular action, user device 210 is to provide a prompt and/or perform another particular action. In this way, user device 210 can provide and/or perform multiple prompts and/or actions.

In some implementations, user device 210 may detect the trigger to provide the particular prompt and/or perform the particular action based on receiving information from a data source. For example, cloud server 220 may monitor one or more data sources (e.g., an air quality data source, a pollen count data source, or the like), and may communicate with user device 210 to indicate that user device 210 is to provide the particular prompt and/or perform the particular action based on monitoring the one or more data sources. Additionally, or alternatively, user device 210 may monitor the one or more data sources, and may detect the trigger based on receiving information from a data source of the one or more data sources. For example, based on parsing the action plan, user device 210 may determine that a patient is to utilize a preventer inhaler when an air quality metric fails to satisfy an air quality metric threshold. In this case, based on receiving information from an air quality data source indicating that the air quality metric fails to satisfy the air quality metric threshold, user device 210 may be triggered to provide a prompt associated with causing a user (e.g., the patient) to utilize the preventer inhaler. Similarly, based on monitoring a social media data source, a search history, or the like, user device 210 may determine that a user is suffering from a particular symptom (e.g., a coughing symptom based on detecting a user search for cough medicine), and may determine based on the action plan to prompt the user to confirm the particular symptom and subsequently provide a recommendation (e.g., to utilize a particular medication).

As further shown in FIG. 4, process 400 may include providing the particular prompt and/or performing the particular action based on detecting the trigger (block 440). For example, user device 210 may provide the particular prompt and/or perform the particular action based on detecting the trigger. In some implementations, user device 210 may cause a user interface to provide the prompt and one or more user interface elements associated with receiving input as a response to the prompt. For example, user device 210 may provide a prompt relating to asthma symptoms, and may provide one or more user interface elements associated with receiving input indicating whether the user is suffering from the asthma symptoms, what type of asthma symptoms the user is suffering from, or the like. Similarly, user device 210 may provide a prompt relating to obtaining a user determination (e.g., prompting the user to determine a result of a peak flow measurement), and may provide a set of user interface elements associated with receiving an indication of the result. In this way, user device 210 improves patient compliance with the action plan and improves a likelihood of positive health outcomes relative to a manually implemented action plan that is not adjusted and/or triggered based on data, such as sensor data, patient responses to prompts, or the like.

In some implementations, user device 210 may provide an alert based on a particular set of permissions. For example, user device 210 may provide a user interface for selecting a set of health care professionals to whom to provide information automatically and/or provide access to medical information. In this case, based on detecting the trigger to provide the particular prompt, user device 210 may select one or more health care professionals to whom permission has been granted to receive health care information, and may provide alerts to the one or more health care professionals. In some implementations, user device 210 may rate a set of health care professionals based on a set of criteria, such as familiarity with the user's symptoms, familiarity with the user's medical history, distance to a corresponding office, schedule availability, or the like. For example, user device 210 may determine that a rating associated with a first health care professional exceeds a rating associated with a second health care professional, and may transmit an alert to the first health care professional. In this way, user device 210 reduces utilization of processor resources by assisting the user in finding the best health care professional more rapidly relative to providing a list of health care professionals to alert and requiring that the user perform manual research to select a particular health care professional.

Additionally, or alternatively, user device 210 may provide a first portion of health information to a first health care professional and a second portion of health information to a second health care professional based on detecting the trigger and the set of permissions. In this way, user device 210 ensures that health care professionals each receive necessary information to ensure positive health outcomes for a patient without the patient being required to manually submit medical information to each health care professional, and without information that is confidential to the patient being provided to a particular health care professional for whom the information is not necessary.

In some implementations, user device 210 may cause the particular action to be performed, such as by transmitting data or the like. For example, user device 210 may transmit information, such as a set of responses to the set of prompts, an alert regarding a condition of a user, or the like, to cloud server 220 to cause cloud server 220 to provide the information to a doctor associated with the action. In this way, user device 210 reduces a likelihood that a doctor lacks information to monitor a patient. Additionally, or alternatively, based on determining that patient usage of an inhaler (e.g., a preventer inhaler or a reliever inhaler) exceeds a threshold rate of usage, user device 210 may classify a user condition as requiring consultation with a doctor (e.g., based on information in the action plan associated with classifying a user condition), and may transmit an alert to a doctor, provide an alert to a user, automatically schedule an appointment for the user with the doctor (e.g., based on obtaining schedules for the user and the doctor), or the like.

Additionally, or alternatively, user device 210 may utilize stored information regarding a prescription to automatically transmit a request for replacement medication (e.g., a refill of the prescription, a different prescription, or the like) based on detecting a trigger indicating that a threshold quantity of medicine has been utilized (e.g., receiving responses to a set of prompts indicating that a user has utilized a threshold quantity of doses). In this way, user device 210 reduces a likelihood that a user experiences negative health outcomes based on lacking sufficient medicine. Moreover, based on utilizing stored data (e.g., prescription information, payment information, or the like), user device 210 reduces an amount of network traffic relative to a user being required to manually locate and order a prescription refill.

Additionally, or alternatively, user device 210 may cause emergency services to be dispatched. For example, based on a combination of multiple triggers (e.g., a rate of usage of a reliever inhaler exceeding a threshold, a heart rate monitor measuring a threshold heart rate, an air quality sensor indicating a threshold air quality value, or the like), user device 210 may classify a condition of a patient as satisfying a threshold classification level, and may cause an ambulance to be automatically dispatched to provide emergency services for the patient based on the condition of the patient satisfying the threshold classification level.

In some implementations, user device 210 may transmit a health summary report to a doctor based on detecting a trigger (e.g., a time trigger). For example, periodically (e.g., daily, weekly, monthly, or the like), user device 210 may generate an alert including a report regarding responses to prompts, sensor data observed, user vitals (e.g., weight, blood pressure, heart rate, blood sugar, etc.), user compliance with a treatment plan included in the action plan, user compliance with medication instructions, or the like, and may transmit the report to another user device 210 utilized by the doctor for review by a doctor. Based on automatically communicating with one or more sensors to obtain the sensor data, the user vitals, or the like, user device 210 may obviate the need for a nurse to utilize medical devices to record user vitals at a doctor's appointment, thereby reducing power consumption by a medical facility.

In some implementations, user device 210 may generate a health score associated with user compliance with the treatment plan portion of the action plan, and may provide the health score for review by a doctor, may provide the health score for display to cause the user to improve compliance (e.g., utilizing a gamification technique), or the like. For example, user device 210 may rate the user based on compliance with the treatment plan (e.g., on a daily basis, a weekly basis, a monthly basis, etc.), and may provide feedback to the user based on rating the user, may provide rewards to the user to incentivize compliance (e.g., a gift card, a charitable donation on the user's behalf, a discount on a medical bill, etc.), or the like. In this way, user device 210 may provide information to improve user compliance with a treatment plan, thereby improving health outcomes relative to a user lacking feedback on compliance. In some implementations, user device 210 may generate an alert, for display to a health care professional, that requires review of the alert prior to dismissal of the alert. For example, a first user device 210 may cause a pop-up to be displayed via a second user device 210 until the pop-up is acknowledged by a user of second user device 210. In this way, user device 210 may ensure that patient information is not ignored by a health care professional.

Additionally, or alternatively, user device 210 may transmit the report to cloud server 220 for automatic analysis. In this case, user device 210 may receive a set of recommendations (e.g., an exercise recommendation, a nutrition recommendation, a dosage recommendation, etc.), a modification to the action plan, an alert for display to the user, or the like based on transmitting the report to cloud server 220 for automatic analysis. Additionally, or alternatively, user device 210 may automatically analyze data of the report, and may generate a set of recommendations for the user based on analyzing the data of the report. For example, based on one or more other action plans that indicate that when a user experienced a particular set of vitals, the one or more other action plans were modified in a particular manner, user device 210 may modify the action plan in the particular manner. Additionally, or alternatively, user device 210 may select a recommendation, of a set of doctor recommendations, and provide the recommendation to the user to modify a behavior of the user and improve a health outcome. In this way, user device 210 may improve health outcomes of a user relative to utilizing a static action plan.

In some implementations, user device 210 may provide information for display based on detecting the trigger. For example, based on detecting a user interaction with a user interface associated with requesting additional information regarding a treatment, a medication, a technique for performing a measurement, or the like, user device 210 may provide information obtained from one or more data sources (e.g., a treatment instruction data source, a pharmaceutical data source, or the like). Additionally, or alternatively, based on stored information indicating that a particular user action is associated with a threshold likelihood of a request for additional information for other users, user device 210 may automatically obtain the information from the one or more data sources and provide the information for display when instructing the user to perform the particular user action. For example, multiple user devices 210 may transmit information to cloud server 220 indicating that corresponding users requested instructions regarding administration of a reliever inhaler. In this case, a particular user device 210 may receive information from cloud server 220 causing the particular user device 210 to automatically obtain and provide the instructions regarding administration of the reliever inhaler without receiving a user request from a corresponding user of the particular user device 210.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5A:
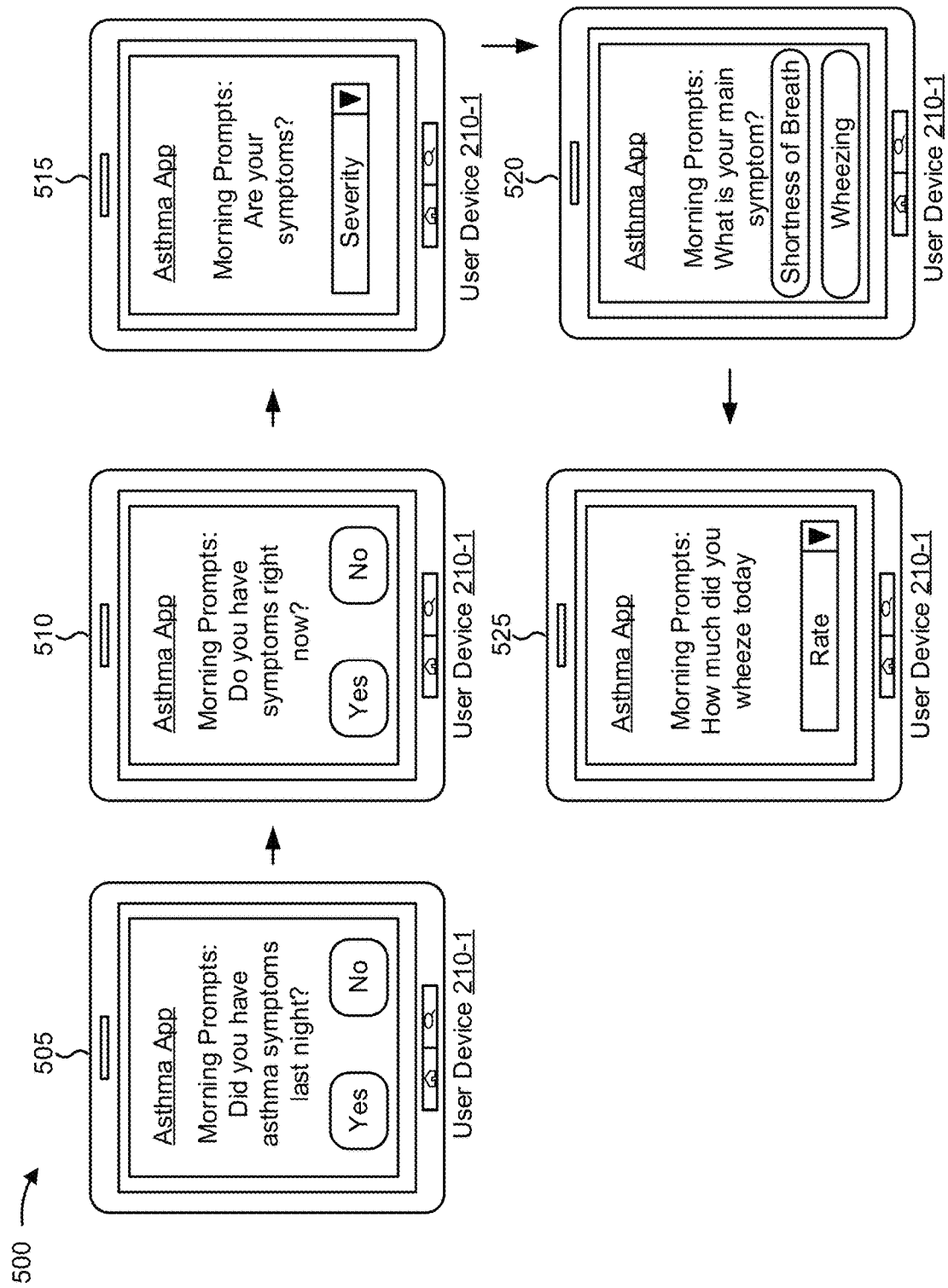
FIGS. 5A and 5B are diagrams of an example implementation relating to the example process shown in FIG. 4.
Figure 5B:
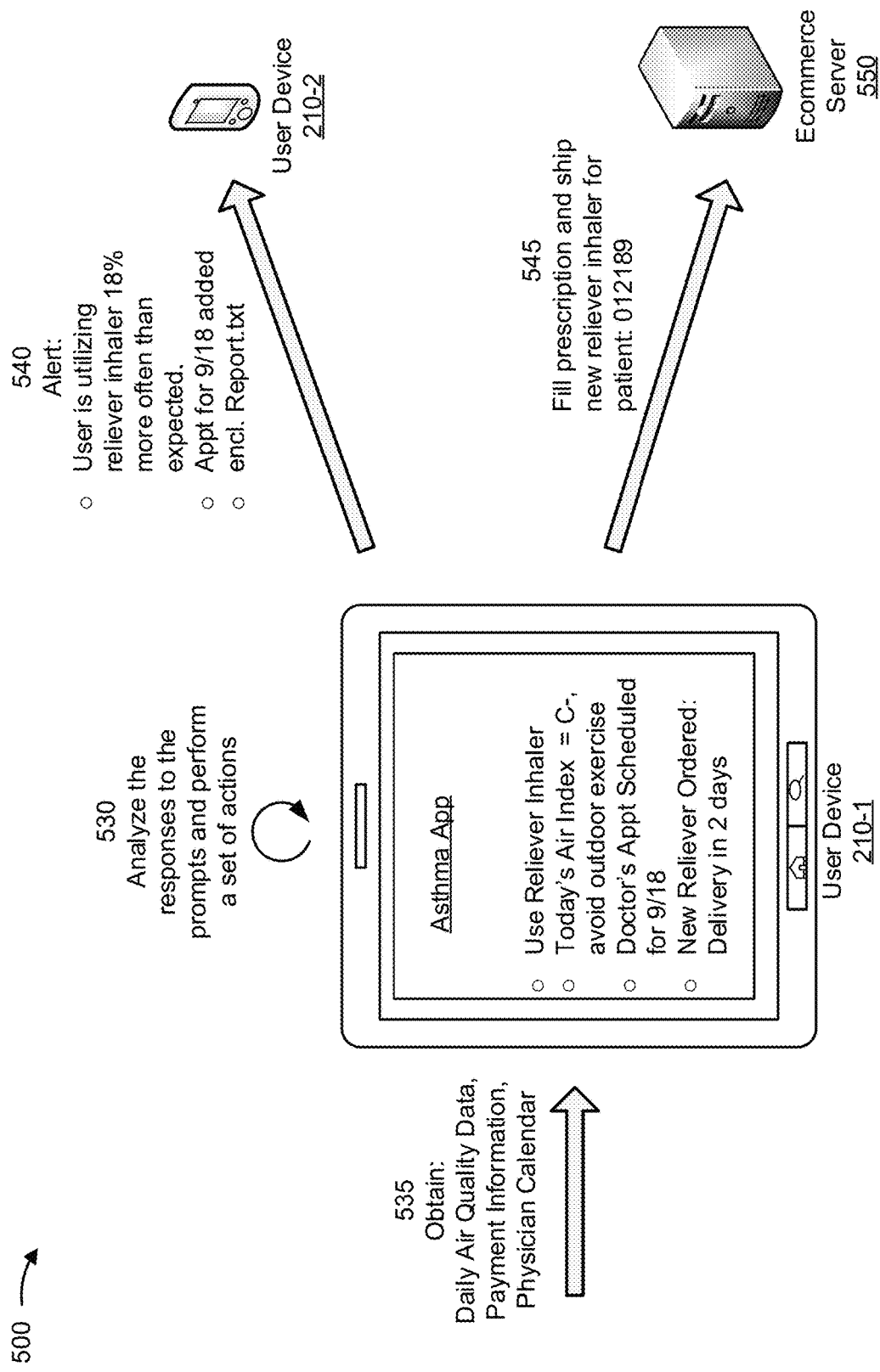

FIGS. 5A and 5B are diagrams of an example implementation 500 relating to example process 400 shown in FIG. 4. FIGS. 5A and 5B show an example of providing device-based action plan alerts.

As shown in FIG. 5A, based on a trigger (e.g., determining that a time for a set of morning prompts has occurred), user device 210 may automatically provide a group of prompts relating to the Asthma Control Questionnaire to assess a status of an asthma patient based on an action plan. As shown by reference number 505, user device 210-1 provides a first prompt regarding whether the asthma patient experienced asthma symptoms during the previous night. Assume that user device 210-1 receives input of a first answer and automatically omits a set of prompts related to receiving a different answer to the first prompt, thereby reducing a quantity of time to complete the group of prompts, a battery utilization associated with providing the group of prompts for display, and/or processing resources associated with providing the group of prompts for display relative to providing all prompts of the group of prompts.

As further shown in FIG. 5A, and by reference number 510, based on receiving the first answer and a relationship between the group of prompts, user device 210-1 provides a second prompt regarding whether the asthma patient is experiencing symptoms. Assume that user device 210-1 receives input of a second answer and automatically omits a set of prompts related to receiving a different answer to the second prompt. As shown by reference number 515, based on receiving the second answer and a relationship between prompts of the group of prompts, user device 210-1 is triggered to provide a third prompt regarding assessing a severity of the asthma patient's symptoms. In some implementations, user device 210-1 may receive input (e.g., voice input, gesture input, or the like) requesting clarification regarding assessing severity, may obtain information from a medical data structure storing guidelines based on receiving the input, and may provide the guidelines for display.

As further shown in FIG. 5A, and by reference number 520, based on receiving input of a third answer indicating a particular severity and the relationship between the group of prompts, user device 210-1 is triggered to provide a fourth prompt regarding identifying a primary symptom (e.g., "shortness of breath" or "wheezing"). Assume that user device 210-1 receives input of a fourth answer indicating that the primary symptom is wheezing and omits a set of prompts relating to receiving an answer of shortness of breath as the primary symptom. As shown by reference number 525, based on the fourth answer and the relationship between prompts of the group of prompts, user device 210-1 provides a fifth prompt regarding how much wheezing the asthma patient experienced. Assume that user device 210-1 receives input indicating a particular rate of wheezing by the asthma patient.

In another example, user device 210 may automate responses to the set of prompts, thereby reducing battery utilization and/or utilization of processor resources relative to providing the prompts for display and detecting user input. For example, user device 210 may utilize a microphone to record audio of the patient's breathing, and may analyze the audio to detect whether a symptom (e.g., wheezing) occurred or is occurring, a severity of the symptom, or the like. Similarly, user device 210 may communicate with a sensor to determine whether a reliever inhaler or preventer inhaler has been utilized by the patient rather than providing a prompt for display to confirm that the reliever inhaler or preventer inhaler has been utilized.

As shown in FIG. 5B, and by reference number 530, user device 210-1 may analyze the responses to the set of prompts and may be triggered to automatically perform a set of actions and provide a set of alerts. As shown by reference number 535, user device 210-1 may communicate with a set of data sources to obtain data, such as daily air quality data, payment information relating to the asthma patient, and a calendar for a doctor of the asthma patient. As shown by reference number 540, user device 210-1 transmits an alert to user device 210-2 that indicates that the asthma patient is utilizing the reliever inhaler more than expected, that identifies an appointment for consulting with the asthma patient, and that includes a report regarding a condition of the asthma patient (e.g., vitals information, inhaler usage information, responses to prompts, or the like). As shown by reference number 545, user device 210-1 transmits data (e.g., a message) to ecommerce server 550 to cause ecommerce server 550 to utilize the payment information to order and ship a new reliever inhaler to the asthma patient. Based on performing the set of response actions, user device 210-1 provides, for display, alert information identifying the response actions, indicating that the user is to utilize the reliever inhaler (e.g., based on the responses to the prompts), and indicating an air quality index (e.g., to advise the user to avoid excessive outdoor activity).

As indicated above, FIGS. 5A and 5B are provided merely as an example. Other examples are possible and may differ from what was described with regard to FIGS. 5A and 5B.

In this way, user device 210 improves data collection for asthma patients and automatically analyzes an action plan to provide alerts regarding a condition of the patient, perform response actions to benefit the patient, or the like. Moreover, based on automatically excluding prompts from a group of prompts, user device 210 reduces a quantity of time to respond to the group of prompts, a battery utilization in providing the group of prompts, and/or a utilization of memory resources to provide the group of prompts relative to providing all prompts via a fixed questionnaire.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
  one or more processors to:
   determine a characteristic of a patient,
     the characteristic relating to an age of the patient;
   customize, based on the characteristic of the patient, a user interface with which to provide an action plan,
     where the user interface is automatically and dynamically adjusted from a pre-configured, standard configuration to a configuration based on the characteristic of the patient;
   provide the user interface to a user device associated with the patient;
   detect one or more interactions with the user interface associated with identifying one or more portions of the action plan,
     the action plan including information regarding a treatment plan for the patient;
   parse the action plan to identify a set of prompts and/or a set of actions that are to be performed based on a set of triggers,
     the set of prompts being related to a clinically validated questionnaire for a particular condition;
   detect, based on receiving sensor data, a particular trigger, of the set of triggers, after parsing the action plan,
     the sensor data being associated with a heartbeat sensor or a motion sensor;
   select, from a group of user interface parameters, a particular set of user interface parameters relating to a presentation of the user interface based on the characteristic relating to the age of the patient;
   provide, for display via the user interface, a particular prompt, of the set of prompts, based on detecting the particular trigger,
     where automatically and dynamically adjusting the user interface from the pre-configured, standard configuration to the configuration based on the characteristic of the patient includes:
generating the user interface based on the particular set of user interface parameters by providing a simplified form of the particular prompt based on the characteristic relating to the age of the patient or increasing a text size of the particular prompt based on the characteristic relating to the age of the patient;
classify a condition of the patient based on detecting the particular trigger,
the condition of the patient satisfying a threshold classification level;
determine a rating associated with each of a plurality of healthcare professionals, including a first healthcare professional and a second healthcare professional, based on a set of criteria; and
transmit an alert regarding the condition of the patient to another device associated with the first healthcare professional,
the alert being displayed on the other device until an interaction is performed with the other device to acknowledge the alert based on the condition of the patient satisfying the threshold classification level, and
the first healthcare professional being selected to receive the alert regarding the condition of the patient based on determining that the rating associated with the first healthcare professional exceeds the rating associated with the second healthcare professional.

2. The device of claim 1, where the one or more processors are further to:
communicate with a set of sensors to obtain the sensor data; and
where the one or more processors, when detecting the particular trigger, are to:
process the sensor data to detect the particular trigger.

3. The device of claim 1, where the one or more processors are further to:
obtain a document identifying a particular portion of the action plan, of the one or more portions of the action plan, based on the one or more interactions with the user interface,
the document being a natural language document;
perform a natural language processing technique on the document to obtain information regarding the action plan; and
where the one or more processors, when parsing the action plan, are to:
parse the information regarding the action plan.

4. The device of claim 1, where the one or more processors are further to:
determine, based on a group of responses to a group of prompts, a utilization of a medication by the patient,
determine that the utilization of the medication indicates that an amount of medication remaining fails to satisfy a threshold amount; and
where the one or more processors, when detecting the particular trigger, are to:
detect the particular trigger based on determining that the utilization of the medication indicates that the amount of medication remaining fails to satisfy the threshold amount.

5. The device of claim 1, where the one or more processors are further to:
detect a particular interaction with the user interface associated with indicating the condition of the patient;
determine that the condition of the patient satisfies a threshold severity; and
transmit data to cause emergency management personnel to be dispatched for the patient based on determining that the condition of the patient satisfies the threshold severity.

6. The device of claim 1, where the condition is an asthma related condition and the clinically validated questionnaire is an Asthma Control Questionnaire; and
where the one or more processors, when providing the particular prompt, are to:
provide the particular prompt to cause the patient to utilize an inhaler.

7. The device of claim 1, where the one or more processors, when customizing the user interface, are to:
customize the user interface by
increasing a size of a button.

8. The device of claim 1, where the sensor data is received from at least one of:
a spirometer,
a quality sensor,
a breath analyzer, or
an accelerometer.

9. A method, comprising:
determining, by a device, a characteristic of an asthma patient,
the characteristic relating to an age of the asthma patient;
customizing, by the device and based on the characteristic of the asthma patient, a user interface with which to provide an action plan,
where the user interface is automatically and dynamically adjusted from a pre-configured, standard configuration to a configuration based on the characteristic of the asthma patient;
receiving, by the device, the action plan,
the action plan being related to monitoring the asthma patient, and
the action plan being associated with a clinically validated questionnaire;
parsing, by the device, the action plan to identify a set of prompts and/or a set of actions,
the set of prompts being related to evaluating the asthma patient based on the clinically validated questionnaire,
the set of actions being related to providing alerts to a set of entities based on evaluating the asthma patient;
detecting, by the device and based on receiving sensor data, a trigger to provide a particular prompt, of the set of prompts or perform a particular action of the set of actions,
the sensor data being associated with a heartbeat sensor or a motion sensor;
selecting, by the device and from a group of user interface parameters, a particular set of user interface parameters relating to a presentation of the user interface based on the characteristic relating to the age of the asthma patient;
providing, by the device, the particular prompt based on detecting the trigger,
where automatically and dynamically adjusting the user interface from the pre-configured, standard configuration to the configuration based on the characteristic of the asthma patient includes:

generating the user interface based on the particular set of user interface parameters by providing a simplified form of the particular prompt based on the characteristic relating to the age of the asthma patient or increasing a text size of the particular prompt based on the characteristic relating to the age of the asthma patient;

classifying, by the device, a condition of the asthma patient based on detecting the trigger,
the condition of the asthma patient satisfying a threshold classification level;

determining, by the device, a rating associated with each of a plurality of healthcare professionals, including a first healthcare professional and a second healthcare professional, based on a set of criteria; and transmitting, by the device, an alert regarding the condition of the asthma patient to another device associated with the first healthcare professional,
the alert being displayed on the other device until an interaction is performed with the other device to acknowledge the alert based on the condition of the asthma patient satisfying the threshold classification level, and
the first healthcare professional being selected to receive the alert regarding the condition of the asthma patient based on determining that the rating associated with the first healthcare professional exceeds the rating associated with the second healthcare professional.

10. The method of claim 9, further comprising:
obtaining, from a data source storing air quality information, an air quality metric;
determining that the air quality metric satisfies an air quality metric threshold;
selecting, based on the action plan, a particular doctor recommendation, of a set of doctor recommendations, related to reducing asthma symptoms relating to the air quality metric satisfying the air quality metric threshold; and
where providing the particular prompt or performing the particular action comprises:
providing, for display via the user interface, the particular doctor recommendation.

11. The method of claim 9, further comprising:
determining, based on a response to the particular prompt, a utilization of an inhaler,
the utilization relating to a quantity of doses included in the inhaler and a quantity of responses, including the response to the particular prompt, indicating the utilization of the inhaler;
determining that the utilization of the inhaler satisfies a threshold; and
automatically causing a replacement inhaler to be ordered for the asthma patient based on determining that the utilization of the inhaler satisfies the threshold.

12. The method of claim 9, further comprising:
storing information relating to the asthma patient,
the information relating to the asthma patient including one or more responses to one or more prompts, the sensor data recorded by the device, and information indicating a compliance with the action plan by the asthma patient; and
where providing the particular prompt or performing the particular action comprises:
transmitting a report for display to the first healthcare professional of the asthma patient,
the report including the information relating to the asthma patient.

13. The method of claim 9, where detecting the trigger comprises:
receiving the sensor data from at least one of:
a spirometer,
a quality sensor,
a breath analyzer, or
an accelerometer.

14. The method of claim 9, where the condition is an asthma related condition and the clinically validated questionnaire is an Asthma Control Questionnaire; and
where providing the particular prompt comprises:
providing the particular prompt to cause the asthma patient to utilize an inhaler.

15. A non-transitory computer-readable medium comprising:
one or more instructions that, when executed by one or more processors, cause the one or more processors to:
determine a characteristic of a patient,
the characteristic relating to an age of the patient;
customize, based on the characteristic of the patient, a user interface with which to provide an action plan,
where the user interface is automatically and dynamically adjusted from a pre-configured, standard configuration to a configuration based on the characteristic of the patient;
provide the user interface to a user device associated with the patient;
detect one or more interactions with the user interface associated with identifying one or more portions of the action plan,
the action plan including information regarding a treatment plan for the patient;
parse the action plan to identify a set of prompts and/or a set of actions that are to be performed based on a set of triggers,
the set of prompts being related to a clinically validated questionnaire for a particular condition;
detect, based on receiving sensor data, a particular trigger, of the set of triggers, after parsing the action plan,
the sensor data being associated with a heartbeat sensor or a motion sensor;
select, from a group of user interface parameters, a particular set of user interface parameters relating to a presentation of the user interface based on the characteristic relating to the age of the patient;
provide, for display via the user interface, a particular prompt, of the set of prompts, based on detecting the particular trigger,
where automatically and dynamically adjusting the user interface from the pre-configured, standard configuration to the configuration based on the characteristic of the patient includes:
generating the user interface based on the particular set of user interface parameters by providing a simplified form of the particular prompt based on the characteristic relating to the age of the patient or increasing a text size of the particular prompt based on the characteristic relating to the age of the patient;
classify a condition of the patient based on detecting the particular trigger,
the condition of the patient satisfying a threshold classification level;

determine a rating associated with each of a plurality of healthcare professionals, including a first healthcare professional and a second healthcare professional, based on a set of criteria; and transmit an alert regarding the condition of the patient to another device associated with the first healthcare professional, the alert being caused to remain displayed on the other device until an interaction is performed with the other device to acknowledge the alert based on the condition of the patient satisfying the threshold classification level, and the first healthcare professional being selected to receive the alert regarding the condition of the patient based on determining that the rating associated with the first healthcare professional exceeds the rating associated with the second healthcare professional.

16. The non-transitory computer-readable medium of claim 15, where the one or more instructions, when executed by the one or more processors, further cause the one or more processors to:

communicate with a set of sensors to obtain the sensor data; and where the one or more instructions, that cause the one or more processors to detect the particular trigger, further cause the one or more processors to:

process the sensor data to detect the particular trigger.

17. The non-transitory computer-readable medium of claim 15, where the one or more instructions, when executed by the one or more processors, further cause the one or more processors to:

obtain a document identifying a particular portion of the action plan, of the one or more portions of the action plan, based on the one or more interactions with the user interface, the document being a natural language document; and perform a natural language processing technique on the document to obtain information regarding the action plan; and where the one or more instructions, that cause the one or more processors to parse the action plan, further cause the one or more processors to:

parse the information regarding the action plan.

18. The non-transitory computer-readable medium of claim 15, where the one or more instructions, when executed by the one or more processors, further cause the one or more processors to:

determine, based on a group of responses to a group of prompts, a utilization of a medication by the patient; and determine that the utilization of the medication indicates that an amount of medication remaining fails to satisfy a threshold amount; and where the one or more instructions, that cause the one or more processors to detect the particular trigger, further cause the one or more processors to:

detect the particular trigger based on determining that the utilization of the medication indicates that the amount of medication remaining fails to satisfy the threshold amount.

19. The non-transitory computer-readable medium of claim 15, where the one or more instructions, when executed by the one or more processors, further cause the one or more processors to:

detect a particular interaction with the user interface associated with indicating the condition of the patient;

determine that the condition of the patient satisfies a threshold severity; and transmit data to cause emergency management personnel to be dispatched for the patient based on determining that the condition of the patient satisfies the threshold severity.

20. The non-transitory computer-readable medium of claim 15, where the condition is an asthma related condition and the clinically validated questionnaire is an Asthma Control Questionnaire; and where the one or more processors, when providing the particular prompt, are to:

provide the particular prompt to cause the patient to utilize an inhaler.

\* \* \* \* \*